US00PP23630P3

(12) United States Plant Patent
Olesen

(10) Patent No.: US PP23,630 P3
(45) Date of Patent: May 28, 2013

(54) CLIMBING ROSE PLANT NAMED 'POULCY019'

(50) Latin Name: *Rosa hybrida*
Varietal Denomination: Poulcy019

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 8 days.

(21) Appl. No.: 13/317,259

(22) Filed: Oct. 13, 2011

(65) Prior Publication Data

US 2013/0097744 P1 Apr. 18, 2013

(51) Int. Cl.
*A01H 5/00* (2006.01)

(52) U.S. Cl.
USPC ..... Plt./115

(58) Field of Classification Search
USPC ..... Plt./115
See application file for complete search history.

*Primary Examiner* — Kent L Bell

(57) ABSTRACT

A new garden rose plant of the climber class which has abundant, dark red flowers and attractive foliage. This new and distinct variety has shown to be uniform and stable in the resulting generations from asexual propagation.

3 Drawing Sheets

Botanical designation: *Rosa hybrida.*
Variety denomination: 'Poulcy019'.

SUMMARY OF THE INVENTION

The present invention constitutes a new and distinct variety of garden rose plant which originated from a controlled crossing between the female seed parent, an unnamed seedling, and the male pollen parent an unnamed seedling.

The two parents were crossed during the summer of 2001 and the resulting seeds were planted in a controlled environment in Fredensborg, Denmark. The new variety, named 'Poulcy019', originated as a single seedling from the stated cross.

The new variety may be distinguished from its parents by flower color and by growth habit.

The objective of the hybridization of this rose variety was to create a new and distinct variety for garden use with unique qualities, such as:

1. Uniform and abundant dark red flowers;
2. Vigorous, but compact growth when propagated both as a budded rose and on its own roots;
3. Exceptional disease resistance.
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy019' from all other varieties of which we are aware.

As part of the rose development program, Mogens N. Olesen germinated the seeds from the aforementioned hybridization during winter of 2001 and conducted evaluations on the resulting seedlings in a controlled environment in Fredensborg, Denmark. 'Poulcy019' was selected in the spring of 2002 by the inventor as a single plant from the progeny of the aforementioned hybridization.

Asexual reproduction of 'Poulcy019' by traditional budding and rooted cuttings was first done by Mogens N. Olesen in the nursery in Fredensborg, Denmark in July, 2002. This initial and other subsequent asexual propagations conducted in controlled environments have demonstrated that the characteristics of 'Poulcy019' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcy019'. Specifically illustrated in the drawing are.

DETAILED DESCRIPTION OF THE VARIETY

Figure 1:
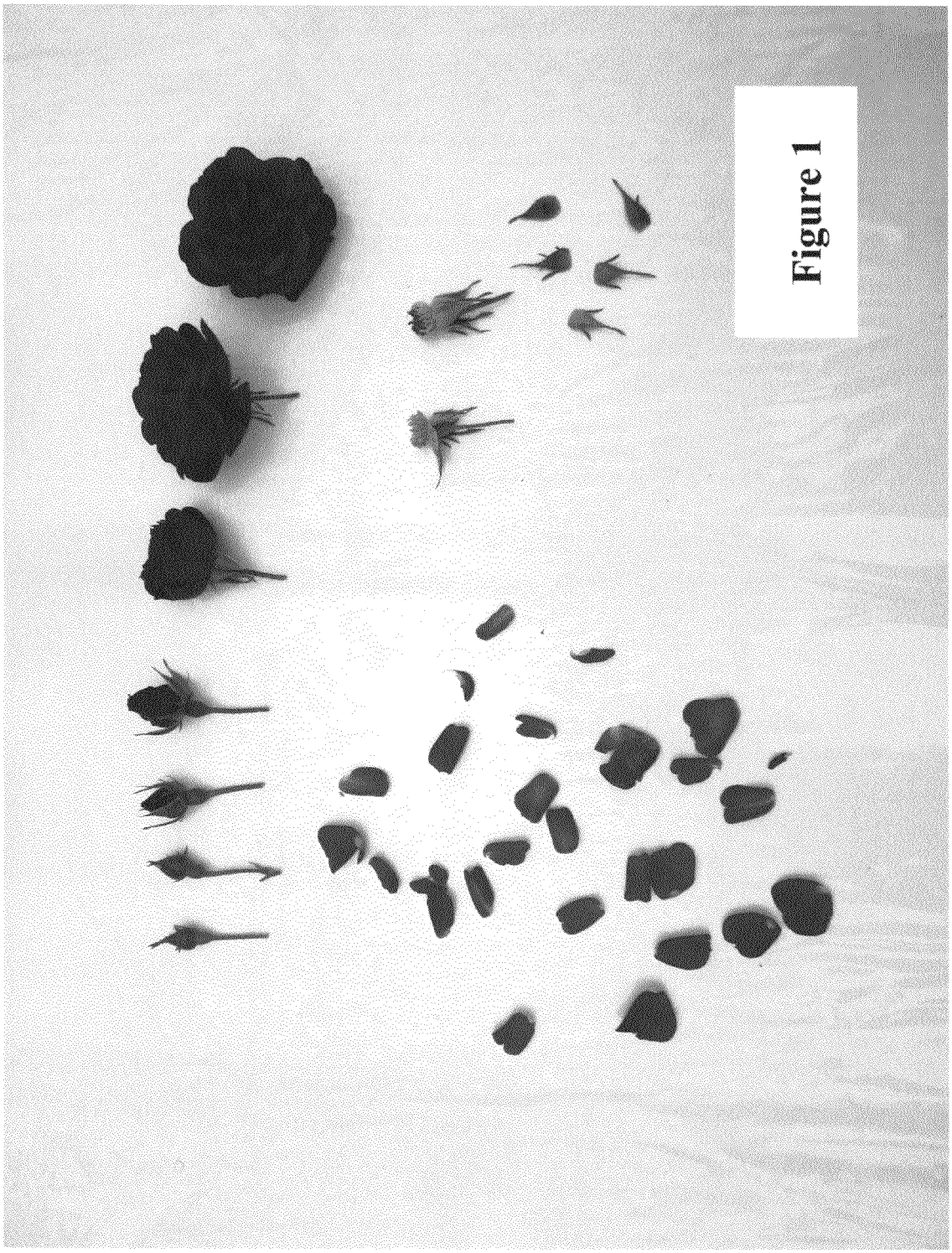
FIG. 1; Open flowers and flower buds with petals and sepals detached.
Figure 2:
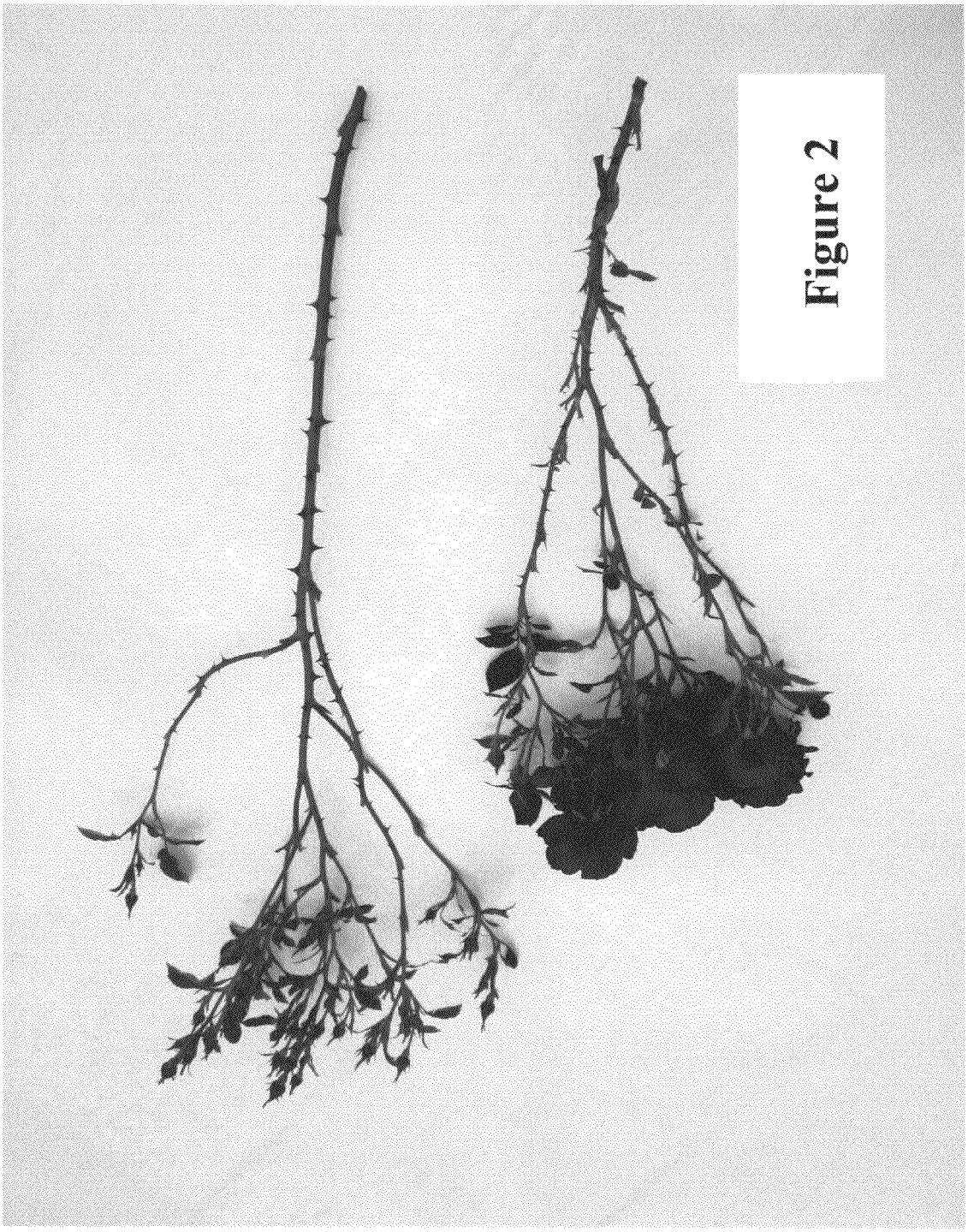
FIG. 2; Flowering stem attached to main branch.
Figure 3:
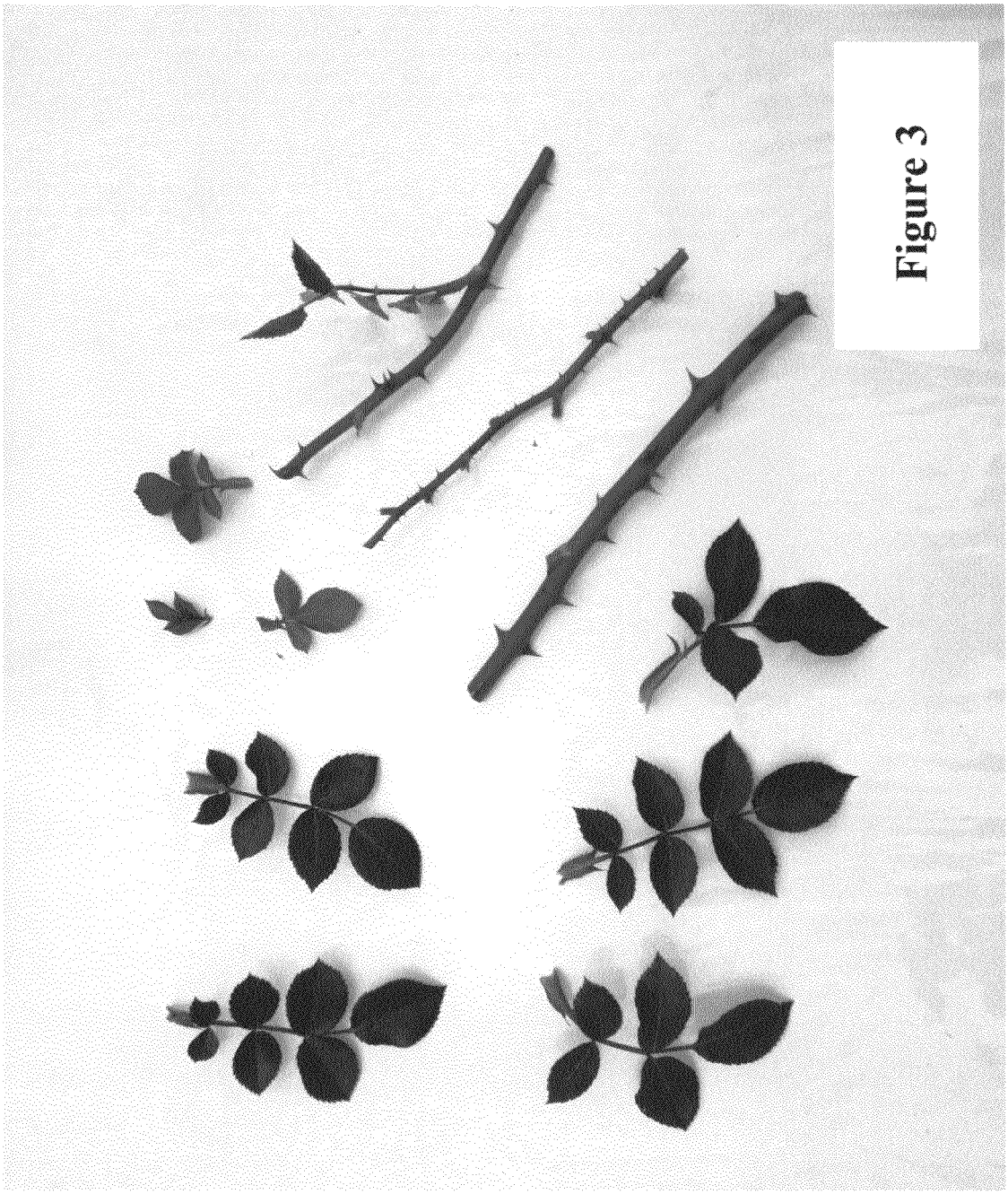
FIG. 3; Leaves and stems.

The following is a description of 'Poulcy019', as observed in its growth in an open air container nursery in Odense, Denmark. Observed plants are 10 months of age, and were grown on own root in 23 cm containers. Color references are made using The Royal Horticultural Society (London, England) Colour Chart, 2001, except where common terms of color are used.

For a comparison, several physical characteristics of the rose variety 'Poulnorm', U.S. Plant Pat. No. 12,552 are compared to 'Poulcy019'. 'Poulcy019' has semi-double, smaller flowers, developing in trusses. 'Poulcy019' is more compact than 'Poulnorm'. 'Poulnorm' has large, double flowers, and develops single flowers on each branch.

FLOWER AND FLOWER BUD

Blooming habit: Early flowering. Stages of continuous periods of bloom.

Flower bud:

*Size.*—Upon opening, 21 mm in length from base of receptacle to end of bud. Bud diameter is 9 mm.

*Bud form*.—Ovoid.

*Bud color*.—As sepals unfold, petals are Red-Purple Group 59A.

*Sepal inner surface*.—Color: Greyed-Green Group 138B. Weak anthocyanin the color of Greyed-Red Group 182A. Surface: Weak pubescence observed.

*Sepal outer surface*.—Color: Green Group 138A. Intense anthocyanic pigments the color of Greyed-Purple Group 183A occasionally covering the entire surface. Texture: Rough.

*Sepal shape*.—Apex: Cirrhose. Base: Flat at union with receptacle.

*Sepal margin*.—Margins have strong weak foliaceous appendages on three of the five sepals.

*Sepal size*.—20 mm long by 7 mm wide.

*Receptacle*.—Texture: Smooth. Shape: Elliptical to campanulate or urn shaped. Size: 7 mm in height by 6 mm wide. Color: Yellow-Green Group 144A. Anthocyanic pigments the color of Greyed-Purple Group 183A observed.

*Peduncle*.—Length: Ranges from 70 to 190 cm. Diameter: 2 to 3 mm. Color: Yellow-Green Group 144A.

*Pedicel*.—Surface: Rough with many stipitate glands. Length: 12 to 16 mm. Diameter: 2 mm on average. Color: Yellow-Green Group 144A. Moderately intense anthocyanic pigments the color of Greyed-Purple Group 183A observed. Strength: Moderate.

Flower bud development: Flower buds are borne in clusters of 12 to 17 flower buds per flowering branch. Reduced apical dominance in flower habit causes flower buds to develop in stages evenly from the base of the plant to the upper branches.

Flower bloom:

*Fragrance*.—Light floral scent.

*Duration*.—The blooms have a duration on the plant of approximately 10 days. Petals fall cleanly away from plant after flowers have fully matured.

*Size*.—Flower diameter is 55 mm on average when open. Flower depth is about 22 mm.

*Flower shape*.—General shape is an open cup with petals that curve out from the flower center.

*Shape of flower, side view*.—After opening the upper portion is flat. The lower portion is flat.

Petalage: On average, flowers have 25 petals total, 0 to 3 of which are petaloids.

Petal color:

*Upon opening, outer petals and inner petals*.—Upper surface: Red Group 46A to 53A. Lower surface: Red-Purple Group 60A.

*Basal petal spots, upon opening*.—Upper surface: Yellow Group 4D. Lower surface: Yellow Group 4D.

*After opening, outer petals and inner petals*.—Upper surface: Red Group 44A. Lower surface: Red-Purple Group 60A.

*Basal petal spots, after opening*.—Upper surface: White Group 155B. Lower surface: White Group 155B.

General tonality: On open flower Red Group 46A. No change in the general tonality at the end of the 10th day.

Petals:

*Petal reflex*.—Somewhat reflexed.

*Margin*.—Entire. Occasionally there is a cleft in the petal apex, or a point at the center of the margin. Medium undulations of margin observed.

*Shape*.—General: Narrow elliptic and broad elliptic. Apex shape: Round. Base shape: Acute.

*Size*.—Outer petals are 30 mm (l)×32 mm (w). Inner petals are 25 mm (l)×18 mm (w).

*Texture*.—Smooth.

*Thickness*.—Average.

Petaloids:

*Quantity*.—0 to 3.

*Shape*.—Asymmetric. Apex is rounded, base is acute.

*Color*.—Upper surface is Red Group 44A. Lower surface is Red-Purple Group 60A.

*Size*.—15 mm in length by 10 mm wide.

Reproductive organs:

*Pollen*.—None observed.

*Anthers*.—Size: 2 mm in length. Color: Yellow-Orange Group 15A. Quantity: 75 on average.

*Filaments*.—Color: Yellow Group 6A. Length: 5 mm.

*Pistils*.—Length: 4 mm. Quantity: 50 on average.

*Stigmas*.—Inferior in location relative to the length of the filaments and the height of the anthers. Color: Greyed White Group 157A.

*Styles*.—Color: Greyed White Group 157A.

*Hips*.—None Observed.

PLANT

Plant growth: Arching. As an own root plant the average height of the plant is 60 cm and the average width is 60 cm.

Stems:

*Color*.—Juvenile growth: Yellow-Green Group 144A with anthocyanic intonations of Greyed-Purple Group 183A. Mature growth: Yellow-Green Group 144A.

*Length*.—On average, canes are 20 cm from the base of the stem to the flowering portion.

*Diameter*.—4 to 5 mm.

*Internodes*.—On mature canes, there is an average distance of 40 to 50 mm between nodes.

*Surface texture*.—Young wood: Rough with small prickles. Older wood: Smooth.

Prickles:

*Incidence*.—12 prickles per 10 cm of stem.

*Size*.—Average length of prickles on mature stems is 6 mm.

*Shape*.—Concave.

*Color*.—Juvenile prickles: Greyed-Purple Group 183A. Mature prickles: Greyed-Red Group 181D.

Plant foliage: Normal number of leaflets per leaf in middle of the stem: 7 leaflets.

*Compound leaf*.—70 to 80 mm (l)×40 to 45 mm (w).

*Quantity*.—3 leaves per 10 cm of stem on average.

*Color of mature foliage*.—Upper side: Green Group 139A. Lower side: Green Group 138A.

*Color of juvenile foliage*.—Upper side: Green Group 137D. Lower side: Green Group 137C. Anthocyanin: Greyed-Purple Group 183A at margins.

Plant leaves and leaflets:

*Stipules*.—Size: 8 to 12 mm in length. Quantity: 2 per compound leaf. Shape: Linear, slightly broad based with outward extending apices. Margins: Finely serrated with few stipitate glands. Color: Yellow-Green Group 144A.

*Petiole*.—Length: 12 to 14 mm. Diameter: 1 mm.

*Upper surface*.—Color: Yellow-Green Group 146A.

*Lower surface*.—Color: Yellow-Green Group 147B.

*Rachis*.—Length: 30 to 35 mm. Upper surface: Yellow-Green Group 146A with anthocyanic pigments the color of Greyed-Purple Group 183A. Lower surface: Yellow-Green Group 144B. Observations: Few stipitate glands and prickles observed.

*Leaflet*.—Margin: Serrate. Size: Terminal leaflet on normal leaves is 20 to 22 mm in length by 12 to 14 mm wide. Shape: Generally elliptic. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery and downy mildew, rust, black spot, and Botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the climbing rose class named 'Poulcy019', substantially as illustrated and described herein, due to its abundant dark red flowers, disease resistance, and extended period of bloom.

* * * * *